United States Patent
Hirano et al.

(10) Patent No.: US 9,212,073 B2
(45) Date of Patent: Dec. 15, 2015

(54) BALLAST WATER TREATMENT AGENT AND METHOD OF TREATING BALLAST WATER OF SHIP USING THE SAME

(71) Applicants: Akihide Hirano, Tokyo (JP); Kotaro Fukuzawa, Tokyo (JP); Kazuki Hayashi, Tokyo (JP); Tetsurou Fukase, Tokyo (JP)

(72) Inventors: Akihide Hirano, Tokyo (JP); Kotaro Fukuzawa, Tokyo (JP); Kazuki Hayashi, Tokyo (JP); Tetsurou Fukase, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 0 days.

(21) Appl. No.: 14/355,365

(22) PCT Filed: Nov. 5, 2012

(86) PCT No.: PCT/JP2012/078635
§ 371 (c)(1),
(2) Date: Apr. 30, 2014

(87) PCT Pub. No.: WO2013/065863
PCT Pub. Date: May 10, 2013

(65) Prior Publication Data
US 2014/0302167 A1    Oct. 9, 2014

(30) Foreign Application Priority Data
Nov. 4, 2011 (JP) ................. 2011-242696

(51) Int. Cl.
*A01N 59/00* (2006.01)
*C02F 1/68* (2006.01)
*C02F 1/76* (2006.01)
*C02F 1/50* (2006.01)
*C02F 103/00* (2006.01)

(52) U.S. Cl.
CPC . *C02F 1/68* (2013.01); *A01N 59/00* (2013.01); *C02F 1/50* (2013.01); *C02F 1/76* (2013.01); *C02F 2103/008* (2013.01); *C02F 2303/04* (2013.01); *C02F 2303/08* (2013.01)

(58) Field of Classification Search
None
See application file for complete search history.

(56) References Cited

U.S. PATENT DOCUMENTS 7,156,882 B2 * 1/2007 Gomez ..................... 8/108.1

FOREIGN PATENT DOCUMENTS

| JP | 52-98638 | 8/1977 |
| JP | 04-322788 A | 11/1992 |
| JP | 04322788 | * 11/1992 |

(Continued)

OTHER PUBLICATIONS

Edited by CSJ, The Chemical Society of Japan, 5th edition Kagaku Benran Oyo Kagaku Hen I, Maruzen Co., Ltd., 1995, pp. 1-646 to 1-647, particularly, p. 1-647, left column, lines 5 to 33.

(Continued)

*Primary Examiner* — Robert A Wax
*Assistant Examiner* — Melissa Mercier
(74) *Attorney, Agent, or Firm* — Posz Law Group, PLC

(57) ABSTRACT

A ships' ballast water treatment agent is obtained by blending phosphate and sodium hydroxide into a hypochlorite solution and has pH of 10 to 13. A blending amount of phosphate is preferably such that a weight ratio of effective chlorine to phosphate acid ($PO_4$) (effective chlorine:phosphate acid) is 30:1 to 2:1. A ships' ballast water treatment agent as such has excellent performance in killing bacteria and microorganisms, such as plankton, included in ships' ballast water and has stability and an anticorrosion property.

16 Claims, 1 Drawing Sheet

(56) References Cited

FOREIGN PATENT DOCUMENTS

| | | | |
|---|---|---|---|
| JP | 2004-537571 A | 12/2004 |
| JP | 2009-297610 A | 12/2009 |
| JP | 2010-013098 A | 1/2010 |
| JP | 2010-207796 A | 9/2010 |
| JP | 2010-536540 A | 12/2010 |
| JP | 2011-092899 A | 5/2011 |
| JP | 2011-098269 A | 5/2011 |
| RU | 2145237 | * | 7/1999 |
| WO | 03/013250 A1 | 2/2003 |
| WO | 2009/023241 A1 | 2/2009 |

OTHER PUBLICATIONS

International Search Report of the International Searching Authority mailed Jan. 8, 2013 for the corresponding international application No. PCT/JP2012/078635 (with English translation).

* cited by examiner

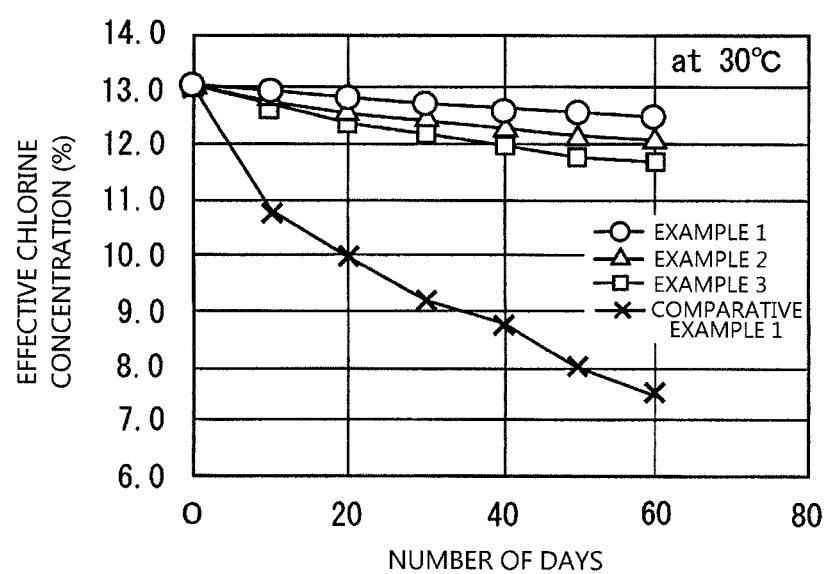

BALLAST WATER TREATMENT AGENT AND METHOD OF TREATING BALLAST WATER OF SHIP USING THE SAME

CROSS REFERENCE TO RELATED APPLICATIONS

This application is a U.S. national stage application of PCT/JP2012/078635 filed on Nov. 5, 2012, and claims priority to, and incorporates by reference, Japanese Patent Application No. 2011-242696 filed on Nov. 4, 2011.

TECHNICAL FIELD

The present invention relates to a treatment agent of ships' ballast water for killing bacteria and microorganisms, such as plankton, included in ships' ballast water loaded in a ballast tank of ships and a treatment method of ships' ballast water using the same, and particularly relates to a treatment agent of ships' ballast water having excellent stability and anticorrosion property and a treatment method of ships' ballast water using the same.

BACKGROUND ART

Ships, specially cargo ships, are generally designed considering to include weight of loaded cargos, etc., therefore, a ship in a state of loaded with no or few cargos takes in sea water at a port before departure to keep balance of the ship for the necessity of securing the propeller immersion depth and navigational safety, etc. during no cargo. The water used as ballast is called ships' ballast water. The ships' ballast water is sea water, etc. loaded to a ballast tank at a port when departing the port with no cargo, while the ships' ballast water is discharged when loading cargos at a port.

When filling and discharging ships' ballast water to and from ships moving between loading ports and unloading ports of different environments, there is a concern of adversely affecting ecosystems of coasts by difference of microorganisms included in the ships' ballast water between the loading port and unloading port. Therefore, at the international convention for the management of ships' ballast water, the international treaty for the Control and Management of Ships' Ballast Water and Sediments was adopted in February of 2004 and a treatment of ships' ballast water became obliged.

The standard of ships' ballast water treatment established by the International Maritime Organization (IMO) is that the number of living organisms of 50 µm or greater (mainly zooplankton) included in ships' ballast water to be discharged from ships is less than 10 per 1 m$^3$, the number of living organisms of 10 µm or greater but smaller than 50 µm (mainly phytoplankton) is less than 10 in 1 ml, the number of cholera is less than 1 cfu per 100 ml, the number of *Escherichia coli* is less than 250 cfu per 100 ml, and the number of Intestinal Enterococci is less than 100 cfu per 100 ml.

To satisfy the treatment standard of ballast water as above, a variety of methods to kill microorganisms in sea water to be filled in a ballast tank have been proposed. For example, the patent article 1 discloses a device for killing microorganisms, etc. by irradiating an ultraviolet ray (UV) after filtering raw water. Also, the patent article 2 discloses a device for killing microorganisms by injecting ozone to ballast water. The patent article 3 discloses a ballast water treatment method of killing microorganisms, etc. by generating electrolytic chlorine by an electrolytic device.

As a method of performing a treatment on microorganisms, etc. in ships' ballast water by using a bactericidal agent, the patent article 4 discloses a ships' ballast water treatment method of killing microorganisms, etc. by adding a chlorine-based bactericidal agent, such as sodium hypochlorite and calcium hypochlorite, to ships' ballast water and securing retention time. Also, the patent articles 5 and 6 disclose treatment devices of ships' ballast water for killing microorganisms, etc. by adding sodium hypochlorite to ships' ballast water. Furthermore, a technique of obtaining a bactericidal agent by generating chlorine dioxide as an oxide from chlorate, hydrogen peroxide and sulfuric acid and a technique of generating peracetic from hydrogen peroxide and acetate and killing with excessive hydrogen peroxide and peracetic have been known.

PRIOR ART DOCUMENTS

Patent Article

[Patent Article 1] Japanese Patent Publication (Kokai) No. 2010-207796
[Patent Article 2] Japanese Patent Publication (Kokai) No. 2010-13098
[Patent Article 3] Japanese Patent Publication (Kokai) No. 2010-536540
[Patent Article 4] Japanese Patent Publication (Kokai) No. 2009-297610
[Patent Article 5] Japanese Patent Publication (Kokai) No. 2011-092899
[Patent Article 6] Japanese Patent Publication (Kokai) No. 2011-098269

DISCLOSURE OF THE INVENTION

Problems to be Solved by the Invention

In the ballast water treatment device described in the patent article 1, however, not only a device for generating an ultraviolet ray but a large amount of electricity is necessary and a power generator has to be provided in many cases. Furthermore, there is a disadvantageous point that a UV lamp has to be cleaned regularly, so that it is troublesome and impractical.

In the ballast water treatment device described in the patent article 2, a device for generating ozone and a large amount of electricity are necessary and a power generator has to be provided in many cases. Furthermore, a costly ozone dissolving tank is necessary and a treatment of waste ozone is required, which are disadvantageous points.

Furthermore, although a ballast water treatment method for killing microorganisms, etc. by generating electrolytic chlorine by an electrolytic device is disclosed in the patent article 3, electrolytic devices are costly and the control is cumbersome, a treatment of a hydrogen gas generated at the same time is required, moreover, a device for the treatment and a large amount of electricity are necessary and a power generator has to be provided in many cases, which are disadvantageous.

Therefore, use of a chemical agents as described in the patent articles 4 to 6 may be considered. Sodium hypochlorite used in the patent articles 4 to 6 is inexpensive and is liquid which is easy to use, so that it is widely used, however, it is unstable at a high temperature and causes autolysis. Therefore, a cooling device has to be provided to keep it at 30° C. or lower and the control is troublesome, which are disadvantageous. On the other hand, calcium hypochlorite used in the patent article 4 causes precipitation of calcium sulfate and forms scales when dissolved in sea water, so that it is necessary to either provide a desalination device or remove scales, which is disadvantageous. Also, these hypochlorites are liable to be autolyzed, and an effective chlorine concentration of 5 to 6 wt % declines after 60 days at 30° C. Autolyzed hypochlorous acid becomes chloric acid after becoming chlorous acid, however, the chloric acid is highly poisonous and is a problem in ballast water discharge.

Also, in the technique of obtaining a bactericidal agent by generating chlorine dioxide as an oxide from chlorate, hydrogen peroxide and sulfate and the technique of generating peracetic from hydrogen peroxide and acetate and killing with excessive hydrogen peroxide and peracetic, there are disadvantageous points that not only are those bactericidal components used therefor expensive but they are very unstable and have to be synthesized on ships immediately before use.

Furthermore, since all of bactericidal agents used in those treatments are oxidizing agents (oxidizing), when adding an amount enough to give the effect of killing plankton, ships' ballast water pipes and ballast tank are corroded in some cases. Such a corrosion problem does not become a problem in the case of ships short after being built because it is painted sufficiently, while in ships after years from being painted, deterioration and cracks of paint arise and the condition is quite vulnerable to corrosion. Therefore, corrosion by those bactericidal agents has been a big problem in existing ships. Particularly, since ballast tanks are often installed on circumferential sides of ships, when corrosion develops, it may possibly cause a flood or other problem, consequently, corrosion of a ballast tank largely affects durability of ships.

As explained above, there has not been any ships' ballast water treatment agent, which exhibits an excellent killing performance, has an excellent anticorrosion property and stability and requires only small store.

The present invention has an object thereof to solve the disadvantages as explained above and to provide a ships' ballast water treatment agent having an excellent performance in killing bacteria and microorganisms, such as plankton, included in ships' ballast water, and having stability and anticorrosion property. Also, the present invention has an object thereof to provide a treatment method of ships' ballast water using the ships' ballast water treatment agent as such.

Means to Solve the Problems

To attain the above objects, firstly, the present invention provides a ships' ballast water treatment agent, wherein phosphate and sodium hydroxide are blended into a sodium hypochlorite solution and a pH is 10 to 13 Invention 1).

According to the invention (Invention 1), bacteria and microorganisms, such as plankton, in ships' ballast water can be killed with hypochlorous acid and corrosion of a ballast tank due to phosphate can be suppressed.

Here, by blending sodium hydroxide to adjust the pH to 10 to 13, autolysis of hypochlorous acid can be suppressed. Thereby, it is possible to obtain a ships' ballast water treatment agent capable of exhibiting a killing performance of bacteria and aquatic microorganisms, such as plankton, as well as excellent stability and anticorrosion.

In the invention above (Invention 1), preferably a weight ratio of effective chlorine derived from the sodium hypochlorite to phosphate acid derived from phosphate is 30:1 to 2:1 (Invention 2).

According to the invention (Invention 2), a sufficient amount of phosphate for anticorrosion property can be dissolved in a sodium hypochlorite solution.

Secondary, the present invention provides a ships' ballast water treatment method of adding to ships' ballast water with a treatment agent obtained by blending phosphate and sodium hydroxide into a sodium hypochlorite solution and having pH of 10 to 13 (Invention 3).

According to the invention (Invention 3), it is possible to kill bacteria and microorganisms, such as plankton, in ships' ballast water by using hypochlorous acid, and corrosion of a ballast tank can be suppressed by phosphate. Here, by blending sodium hydroxide to adjust the pH to 10 to 13, autolysis of hypochlorous acid can be suppressed. Thereby, it is possible to attain a ships' ballast water treatment method, by which a killing performance of bacteria and aquatic microorganisms, such as plankton, included in ships' ballast water can be brought out and excellent stability and anticorrosion can be obtained.

Effect of the Invention

According to the ships' ballast water treatment agent of the present invention, hypochlorous acid is used for killing bacteria and aquatic microorganisms, such as plankton, in ships' ballast water and corrosion of ballast tank due to phosphate can be suppressed. When adjusting the pH by blending sodium hydroxide here, autolysis of hypochlorous acid can be suppressed.

BRIEF DESCRIPTION OF DRAWINGS

FIG. 1 A graph showing changes of an effective chlorine concentration over time when ships' ballast water treatment agents of examples 1 to 3 and comparative example 1 were kept at 30° C.

MODE FOR CARRYING OUT THE INVENTION

A ships' ballast water treatment agent of the present embodiment is obtained by blending phosphate and sodium hydroxide into a sodium hypochlorite solution, and a pH thereof is 10 to 13.

As the above sodium hypochlorite solution, those containing 1 to 30 wt % of effective chlorine may be used, however, when an effective chlorine concentration is too low, an amount to be loaded becomes too large, so that the effective chlorine concentration is preferably 8 wt % or higher and particularly those having a high effective chlorine concentration of 12 wt % or higher are preferable for reducing the load amount. As the sodium hypochlorite, there are low-sodium products and normal products but either of them may be used as salt does not affect efficacy of the agent.

Also, as phosphate, orthophosphate, monobasic sodium phosphate, disodium phosphate, trisodium phosphate, sodium tripolyphosphate, sodium polymetaphosphate and other sodium phosphates may be used alone or in combination of two or more kinds. Also, potassium phosphates and other phosphates may be also used in the same way as sodium phosphates.

Also, in the present embodiment, metal zinc may be added as a sacrificial electrode. A form of metal zinc is not particularly limited and a plate shape, granular shape and powder shape of zinc may be used. For anticorrosion, since it is necessary to dissolve zinc in a certain amount or more, the adding amount can be less with granular shape having a large surface area. On the other hand, it is easy to use plate-shaped zinc in terms of practical use. Note that in the present specification, metal zinc is not limited to pure zinc and zinc alloys containing at least 50%, particularly, at least 70% of zinc are also included.

As explained above, in the ships' ballast water treatment agent of the present embodiment composed of various components as explained above, a blending amount of phosphoric acid is 1 to 50 mg/L and preferably 2.5 to 10 mg/L when metal zinc as a sacrificial electrode is provided. It is 3 to 100 mg/L and preferably 5 to 50 mg/L when metal zinc is not added. A concentration of sodium hypochlorite (in terms of effective chlorite concentration) for killing living organisms in ballast water is 5 mg/L or higher and preferably 10 mg/L or higher. When calculating from these concentrations, a blending amount of phosphate becomes 30:1 to 2:1 in a weight ratio of effective chlorine to phosphoric acid ($PO_4$) (effective chlorite:phosphate). Specifically, phosphate may be blended by 0.4 to 6.5 wt % in the case of a sodium hypochlorite solution having an effective chlorine concentration of 13 wt %.

Also, when adding metal zinc, an amount thereof may be set such that a zinc elution amount as a current value becomes 5 to 50 $mA/m^2$. When the current value is 5 $mA/m^2$ or smaller, the reducing effect as the anticorrosion agent is not sufficient while when exceeding 50 $mA/m^2$, zinc will be wasted, which is not favorable.

In a ships' ballast water treatment agent based on the sodium hypochlorite solution as above, sodium hydroxide is added to adjust the pH to 10 to 13. This is because of the reason below.

Namely, when the pH is lower than 10, not only does it become difficult to suppress autolysis speed of hypochlorous acid but also the killing performance declines. Also, a necessary phosphoric acid concentration to attain the ratio of sodium hypochlorite to phosphoric acid of 2:1 or more is 7.5 wt % when the sodium hypochlorite contains 15 wt % of effective chlorine. The pH has to be 10 or higher to dissolve this amount of phosphate. On the other hand, a sodium hypochlorite solution having an effective chlorine concentration of 13 wt % or higher normally has a pH of 12 to 14, however, phosphate cannot be dissolved enough for anticorrosion purpose in a sodium hypochlorite solution having a pH of 14. For example, trisodium phosphate is hardly dissolved. On the other hand, in a sodium hypochlorite solution having a pH of 13, 1 wt % or more of phosphate can be dissolved at normal temperature. Note that when using orthophosphate as a phosphoric acid source, 10 wt % or more phosphate can be dissolved, however, the pH becomes acidic and hypochlorous acid autolyzes rapidly. Based thereon, a pH of the ships' ballast water treatment agent of the present embodiment is specified to be 10 to 13. Note that when adjusting the pH, in addition to sodium hydroxide, hydrochloric acid (HCl) may be also used according to circumstances.

As explained above, an adding amount of the ships' ballast water treatment agent of the present embodiment as explained above to ships' ballast water may be such that sodium hypochlorite becomes 5 to 100 mg/L or so (in terms of effective chlorine concentration), particularly 30 to 50 mg/L or so. Note that an adding amount of the treatment agent may be adjusted suitably in accordance with an amount of organic substances (DOC and POC, etc.) and an ammonia concentration in the ships' ballast water.

EXAMPLES

Below, the present invention will be explained furthermore in detail with specific examples.

Examples 1 to 4 and Comparative Example 1

Monobasic sodium phosphate was blended in a sodium hypochlorite solution having an effective chlorine concentration of 13 wt % in an amount of 1 L such that a ratio (weight ratio) of phosphoric acid to effective chlorine becomes as shown in Table 1. This solution is added with granular NaOH gradually to change the pH to 10, 11, 12, 12.5 and 13 to adjust ships' ballast water treatment agents, respectively, and it was observed whether or not there was any undissolved residue (solubility). Also, it was evaluated that whether a sufficient killing performance and anticorrosion property were exhibited or not when diluting these ships' ballast water treatment agents 4800 times. The results are shown in Table 1.

Also, for comparison, on the case of a sodium hypochlorite solution only and not added with any monobasic sodium phosphate (comparative example 1), the same observation of undissolved residue and evaluations on a killing performance and anticorrosion property were made. The results are shown in Table 1.

Furthermore, a ships' ballast water treatment agent with a pH of 12.5 in the example 1, that with a pH of 11 in the example 2, that with a pH of 10 in the example 3 and that with a pH of 13 in the comparative example 1 were kept at 30° C. for 60 days and changes of effective chlorine concentrations were measured. The results are shown in FIG. 1.

TABLE 1

|  |  | Example 1 | Example 2 | Example 3 | Example 4 | Comparative Example 1 |
|---|---|---|---|---|---|---|
| Mix Ratio (Weight Ratio) | Chlorine | 30 | 30 | 30 | 30 | 30 |
|  | Phosphate Acid | 1 | 6 | 15 | 20 | — |
| pH 10 | Killing Performance | ◯ | ◯ | ◯ | ◯ | ◯ |
|  | Anticorrosion Property | ◯ | ◯ | ◯ | ◯ | X |
|  | Solubility | ◯ | ◯ | ◯ | Δ | ◯ |
| pH 11 | Killing Performance | ◯ | ◯ | ◯ | ◯ | ◯ |
|  | Anticorrosion Property | ◯ | ◯ | ◯ | ◯ | X |
|  | Solubility | ◯ | ◯ | Δ | Δ | ◯ |
| pH 12 | Killing Performance | ◯ | ◯ | ◯ | ◯ | ◯ |
|  | Anticorrosion Property | ◯ | ◯ | ◯ | ◯ | X |
|  | Solubility | ◯ | Δ | Δ | Δ | ◯ |

TABLE 1-continued

|  |  | Example 1 | Example 2 | Example 3 | Example 4 | Comparative Example 1 |
|---|---|---|---|---|---|---|
| pH 12.5 | Killing Performance | ○ | ○ | ○ | ○ | ○ |
|  | Anticorrosion Property | ○ | ○ | ○ | ○ | XX |
|  | Solubility | ○ | Δ | Δ | Δ | ○ |
| pH 13 | Killing Performance | ○ | ○ | ○ | ○ | ○ |
|  | Anticorrosion Property | ○ | ○ | ○ | ○ | X |
|  | Solubility | ○ | Δ | Δ | Δ | ○ |

Killing Performance
○: sufficient killing performance
Δ: slightly inferior killing performance
X: insufficient killing performance
Anticorrosion Property
○: sufficient anticorrosion property
Δ: slightly inferior anticorrosion property
X: insufficient anticorrosion property
Solubility
○: no residue
Δ: some residue
X: lots of residue As is clear from Table 1, all of the ships' ballast water treatment agents of examples 1 to 4 and comparative example 1 have sufficient killing performance, however, the ships' ballast water treatment agent in the comparative example 1 exhibited insufficient anticorrosion property. Also, when a blending amount of monobasic sodium phosphate is large, it is not dissolved fully and remains when the pH becomes higher. Therefore, it is understood to be preferable that the pH is adjusted in accordance with a blending amount of monobasic sodium phosphate.

Also, from the results in FIG. 1, in the ships' ballast water treatment agents in examples 1 to 3, an effective chlorine concentration could have been maintained within a decline of not more than 1.5 wt % or so also after being kept for 60 days, while in the ships' ballast water treatment agent in comparative example 1, it declined by 5 wt % or more. Therefore, it was confirmed that the ships' ballast water treatment agents in examples 1 to 3 were excellent in stability.

INDUSTRIAL APPLICABILITY

The ships' ballast water treatment agent of the present invention can be used suitably for a treatment of ships' ballast water of a variety of ships, particularly large ships.

The invention claimed is:

1. A method of treating ballast water of a ship, comprising:
blending phosphate and sodium hydroxide in a sodium hypochlorite solution to obtain a treatment agent, which has a pH of 10 to 13; and
adding the treatment agent to the ballast water of the ship.

2. The method of claim 1, wherein the treatment agent further comprises a ratio of effective chlorine to phosphoric acid ranging from about 30:1 to about 2:1.

3. The method of claim 1, wherein the treatment agent further comprises a weight percentage of effective chlorine ranging from about 1 wt % to about 30 wt %.

4. The method of claim 3, wherein the treatment agent further comprises a weight percentage of effective chlorine greater than about 8%.

5. The method of claim 3, wherein the treatment agent further comprises a weight percentage of effective chlorine is greater than about 12%.

6. The method of claim 1, wherein the treatment agent further comprises zinc.

7. The method of claim 6, wherein the treatment agent further comprises a concentration of phosphoric acid ranging from about 1 to about 50 mg/L.

8. The method of claim 7, wherein the treatment agent further comprises a concentration of phosphoric acid ranging from about 2.5 to about 10 mg/L.

9. The method of claim 6, wherein the treatment agent further comprises a concentration of phosphoric acid ranging from about 3 to about 100 mg/L.

10. The method of claim 7, wherein the treatment agent further comprises a concentration of phosphoric acid ranging from about 5 to about 50 mg/L.

11. The method of claim 7, wherein the treatment agent further comprises a concentration of sodium hypochlorite is at least about 5 mg/L, in terms of effective chlorine.

12. The method of claim 11, wherein the treatment agent further comprises a concentration of sodium hypochlorite is about 10 mg/L, in terms of effective chlorine.

13. The ships' ballast water treatment method of claim 6, wherein the zinc has an elution amount between about 5 to about 10 mA/m$^2$.

14. The ships' ballast water treatment method of claim 6, wherein the treatment agent further comprises a ratio of effective chlorine to phosphate acid is about 30:1.

15. The ships' ballast water treatment method of claim 6, wherein the treatment agent further comprises a ratio of effective chlorine to phosphate acid is about 30:6.

16. The ships' ballast water treatment method of claim 6, wherein the pH of the treatment agent is between about 10 and 11.

* * * * *